(12) United States Patent
Walzman

(10) Patent No.: US 10,548,607 B2
(45) Date of Patent: *Feb. 4, 2020

(54) MESH CAPS

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/024,673

(22) Filed: Jun. 29, 2018

(65) Prior Publication Data

US 2018/0317934 A1    Nov. 8, 2018

Related U.S. Application Data

(63) Continuation-in-part of application No. 15/732,519, filed on Nov. 20, 2017.

(60) Provisional application No. 62/600,134, filed on Feb. 13, 2017.

(51) Int. Cl.
*A61B 17/12* (2006.01)
*A61M 25/00* (2006.01)
*A61M 25/10* (2013.01)
*A61B 90/00* (2016.01)

(52) U.S. Cl.
CPC .... *A61B 17/12172* (2013.01); *A61B 17/1219* (2013.01); *A61B 17/12036* (2013.01); *A61B 17/12113* (2013.01); *A61B 17/12145* (2013.01); *A61B 17/12177* (2013.01); *A61M 25/0021* (2013.01); *A61B 17/1214* (2013.01); *A61B 17/12186* (2013.01); *A61B 2017/1205* (2013.01); *A61B 2090/3966* (2016.02); *A61M 25/10* (2013.01); *A61M 2025/0042* (2013.01); *A61M 2025/1047* (2013.01); *A61M 2210/12* (2013.01)

(58) Field of Classification Search
CPC ........ A61B 17/12109; A61B 17/12031; A61B 17/1214; A61B 17/12113; A61B 17/12172; A61B 17/12; A61B 17/12177
USPC ........................................................ 606/200
See application file for complete search history.

(56) References Cited

U.S. PATENT DOCUMENTS

| | | |
|---|---|---|
| 3,874,388 A | 4/1975 | King et al. |
| 4,282,875 A | 8/1981 | Serbinenko |
| 4,346,712 A | 8/1982 | Handa et al. |
| 4,402,319 A | 9/1983 | Handa et al. |
| 4,619,246 A | 10/1986 | Molgaard-Nielsen et al. |
| 4,675,361 A | 6/1987 | Ward, Jr. |
| 5,165,421 A | 11/1992 | Fleischhacker et al. |
| 5,263,963 A | 11/1993 | Garrison et al. |
| 5,334,210 A | 8/1994 | Gianturco |
| 5,733,294 A | 3/1998 | Forber et al. |
| 5,907,893 A | 6/1999 | Zadno-Azizi et al. |
| 6,221,086 B1 | 4/2001 | Forber |
| 6,375,670 B1 | 4/2002 | Greenhalgh |
| 6,605,102 B1 | 8/2003 | Mazzocchi et al. |

(Continued)

FOREIGN PATENT DOCUMENTS

WO    WO2011/057002 A2    5/2011

*Primary Examiner* — George J Ulsh

(57) ABSTRACT

The present invention teaches the use of a disc shaped mesh intrasaccular occlusion structure with at least one hole in said disc, with optional supplemental hydrogel, which is designed to implement an endovascular treatment to facilitate saccular aneurysm treatment while ameliorating or eliminating aneurysm recurrence.

13 Claims, 6 Drawing Sheets

(56) References Cited

U.S. PATENT DOCUMENTS

| | | |
|---|---|---|
| 7,575,582 B2 | 8/2009 | Gandhi et al. |
| 2004/0087998 A1* | 5/2004 | Lee .................. A61B 17/12022 606/200 |
| 2006/0293612 A1* | 12/2006 | Jenson ............... A61B 17/3207 600/585 |
| 2007/0078480 A1* | 4/2007 | Belenkaya ....... A61B 17/12022 606/200 |
| 2008/0033341 A1 | 2/2008 | Grad |
| 2010/0069948 A1 | 3/2010 | Veznedaroglu et al. |
| 2010/0087709 A1* | 4/2010 | Bertolero ........... A61B 1/00142 600/116 |
| 2011/0144669 A1* | 6/2011 | Becking ........... A61B 17/12022 606/158 |
| 2011/0152993 A1* | 6/2011 | Marchand ........ A61B 17/12022 623/1.2 |

* cited by examiner

MESH CAPS

CROSS-REFERENCE(S)

This is a continuation-in-part application claiming the benefit of priority to U.S. Non-Provisional application Ser. No. 15/732,519 filed Nov. 20, 2017, and Prov. Appl. Ser. Nos. 62/600,134 filed Feb. 2, 2017, and 62/497,851 filed Dec. 5, 2016, the entire contents of which are incorporated by reference.

EXAMINER/ART UNIT n/a

DATE APPL. FILED

Jun. 29, 2018

FIELD OF THE INVENTION

The described invention relates generally to endovascular devices generally and more particularly to a specifically a mesh capped disc with at least one central hole.

BACKGROUND OF THE INVENTION

The present invention relates to an endovascular device for filling of a vascular pathology, or other pathologic outpouchings, such as an intracranial aneurysm.

Present actions for ameliorating cerebral aneurysms is performed by either an open surgical clipping of the aneurysm or via interventional endovascular procedures. The most typical of such procedures involves the placement of one or more coils within the aneurysmal sac via a microcatheter. The primary limitation associated with said procedures is the fact so called "wide-necked" aneurysms are not generally amenable to this type of treatment due to the likelihood that the devices associated with said procedures will be displaced from the aneurysm sac. Another limitation associated with procedures which use a single thread coil device is that said device usually requires the surgeon to pack said coil within the aneurysm and thereby increasing the risk of damaging both the vessel and the aneurysm walls.

The prior art discloses the use of intracranial stents that have been developed for placement in the parent blood vessel to act as a buttress for holding the coil(s) in place within the aneurysmal sac in an effort to improve the retention of coils in aneurysms exhibiting such wide-necked anatomy. The fact that said stents must be placed in the brain is a limitation to this approach, due to the medical difficulties associated with damaging the blood vessels of the brain and increasing morbidity in both the short term as well as resulting in post-operative intracranial stenosis. Additionally, placement of such stents requires the use of oral dual antiplatelet therapy, to prevent in-stent thrombosis. The medications have potential bleeding complications. Furthermore, these medications are relatively contraindicated in the setting of a ruptured intracranial aneurysm, which often precludes the use of such stents in these settings.

While the prior art discloses the use of self-expanding coils such as US20100069948A1—Erol Veznedaroglu, said prior art discloses fail to provide a structure which decreases the permeability of blood across the neck of the aneurysm, thus resulting in higher rates of coil compaction within said aneurysm, and aneurysmal recurrence with its attendant risks. The present invention employs a mesh element, positioned predominantly across the neck of the aneurysm/outpouching to surmount said limitation.

While the prior art discloses the use of a self-expanding mesh disc, positioned across the neck of aneurysm, for example U.S. patent application Ser. No. 15/732,519 (Walzman '519), said prior-art disclosures fail to provide a structure which is immediately stabilized due to the lack of positioning elements suitable for gripping the aneurysmal wall. This lack of immediately stabilizing capability can result in the displacement of the device, thus necessitating the closing of said device, reposition of said device and redeployment of said device. Said closing, repositioning and redeploying takes time (when time is usually of the essence when dealing with aneurisms) and tends to damage vessel walls. Additionally, if said mesh disc apparatus is displaced after additional coils are deployed, repositioning of said apparatus may not be possible, and the malposition may result in permanent injury to the patient. The present invention employs mesh element as well as components that secure its position with said aneurysm before detachment, and before placement of additional embolic materials when needed, to surmount said limitation. Thus, a self-expandable aneurysm filling device the can both cover the neck of an aneurysm and serve as a permanent embolic plug in the aneurysm is desirable which is immediately stabilized. The present invention meets these and other needs. Thus, a self-expandable aneurysm filling device the can both cover the neck of an aneurysm and serve as a permanent embolic plug in the aneurysm, with elements that promptly stabilize its position, with the mesh component in its desired position across the neck of the aneurysm, but not projecting into the parent vessel, is desirable. The present invention meets these and other needs.

GENERAL DESCRIPTION

The present invention combines a disc disclosed in Walzman '519 with at least one hole in the disc disclosed in '519. In the preferred embodiment said at least one hole is centrally located in a mesh disc. In some embodiments said at least one hole is located on the periphery of a mesh disk.

The advantage of said at least one hole is they will provide a structure by which the mesh disc of the current invention can be penetrated after achieving immediate and effective stable positioning, by the mesh disc gripping the wall of the aneurysm, with the mesh portion optimally positioned at the neck of the aneurysm. Said at least one hole in the mesh disc will allow other medical devices to access the target aneurysm. The prior art, however, teaches essentially spherical or ovoid configurations of coil and more effective dome-like shape and dense, somewhat flattened mesh at the bottom (neck of the aneurysm) proximal to the distal end of the catheter but they do not have holes in them to allow other medical devices to access the target aneurysm.

SUMMARY OF THE INVENTION

Briefly, and in general terms, the present invention provides for a self-expandable aneurysm-filling device for treatment of an aneurysm, and a system and method for deploying the self-expandable aneurysm filling device into the aneurysm from a parent vessel for treatment of the aneurysm to at least partially fill and stabilize the aneurysm. In one aspect, the system provides a self-expandable aneurysm filling device that can cover the neck of an aneurysm and can act as a permanent embolic plug in the aneurysm. The self-expandable aneurysm-filling device also provides a single, unified complex matrix that expands as it is deployed and achieves a generally half-spherical or semi-ovoid configuration, or other shapes such as pyramidal, kidney-shaped, bi-lobed, or other complex shapes, so that the self-expandable aneurysm-filling device can be secured promptly in its desired position within the aneurysm. The self-expandable aneurysm filling device can be used to independently to mechanically stabilize an aneurysm or be used as an anchor for other embolic devices as well as hydrogel.

The optional configuration of the mesh disc of the device of the present invention can have a single layer, or be multi-layered. Other, optional embodiments of the mesh disc, in some iterations, include a central donut hole within it, to allow an easier access point for subsequent placement of additional embolic material, when desired. When present, said donut hole, in some iterations, can have its edges dimpled inward, to allow a cone-like region to facilitate reentry into the aneurysm.

The mesh disc of the current invention is also detachable from the delivery wire, hypotube or microcatheter. In some iterations said microcatheter can extend through said disc near the distal end of said microcatheter, so that said microcatheter/hypotube can also subsequently serve directly as a route to deliver additional embolic materials into said aneurysm.

The present invention provides for a self-expandable aneurysm-filling device which is capable of immediately stabilization within moments of deployment. In some iterations, however, the at least one hole is two holes which may separated on the mesh disc to allow two medical devices to access the target aneurysm. The present invention includes a self-expandable aneurysm filling device having a compressed undeployed configuration and an expanded three-dimensional deployed configuration, a delivery element (such as a wire or hypotube/microcatheter), and a severable deployment system including a junction capable of releasing said self-expandable aneurysm filling device. The aneurysm filling element of the present invention, in the preferred embodiment, is constructed of a metal such as platinum or platinum alloys, nitinol, and/or other biocompatible metals. The severable deployment element may be mechanically, electrolytically, or thermally, hydrostatically, chemically, or otherwise severed to separate the self-expandable aneurysm filling device from the delivery element.

These and other aspects and advantages of the invention will become apparent from the following detailed description and the accompanying drawings, which illustrate by way of example the features of the invention.

BRIEF DESCRIPTION OF THE DRAWINGS

FIG. 3 also depicts an embodiment in which the delivery microcatheter 13 is a microcatheter capable of acting as a conduit for delivery of coils through it.

FIG. 3A also depicts an embodiment in which the delivery microcatheter 13 is a microcatheter capable of acting as a conduit for delivery of coils through it.

DETAILED DESCRIPTION OF THE INVENTION

Figure 1:
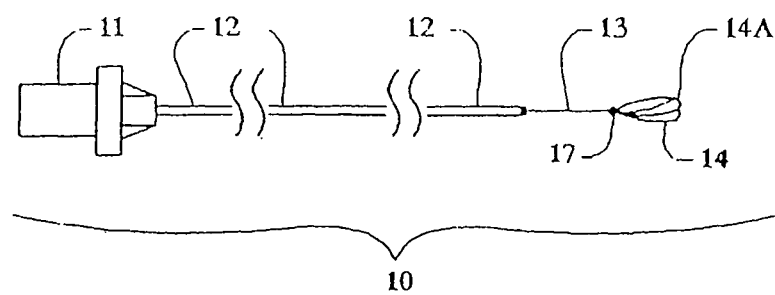
FIG. 1 depicts the present invention 10, including control element 11, catheter element 12 (in cutaway), delivery microcatheter element 13, detachment element 17, and a compressed, flexible mesh disc 14 with peripheral lips 14A, suitable for delivery through microcatheter element 13 and expanded upon release from constraint.

The present invention can be used with or without hydrogel 16. It should be noted that all hydrogels can optionally expand to a specific external stimulus only, rather than time of hydration. And can potentially shrink to an optional external stimulus. This on-demand expansion and shrinkage is helpful for repositioning medical tools near target areas inside veins and arteries. Said external stimuli include, but are not limited to, thermal, electrical, and/or chemical signals. It should also be noted that hydrogel 16 can optionally be radio-opaque, which facilitates remote locating and positioning of said hydrogel 16.

For the treatment of saccular aneurysms: an endovascularly deployed mesh (metal mesh or other mesh) disc—which will optionally have two layers, like the inner disc of the Anplatz Left Atrial Appendage closure device currently in trials. The disc can have versions that are relatively flat, or some versions where the edges are folded up to accommodate differently shaped aneurysms, including very wide neck aneurysms. Such deviations from the generally flat plane of the mesh disc 14 of the current invention may have turned-up sides which conform to the walls of a target aneurysm 100 which are proximal to the aneurysmal neck. Said upturned elements 14A (sometimes referred to as "lips") are optional and optimally used for very wide neck aneurysms that are less spherical in shape and more cylindrical in shape. With said more wide-neck aneurysms the anatomy does not lend itself to the deployment of a flat mesh disc 14 and at least one hole 200 in said mesh disc, because wide neck aneurysms lack sufficient overhang regions at the neck to support the mesh disc.

Without such support said mesh disc 14 and at least one hole 200 in said mesh disc will be dislodged into the parent artery. The present invention teaches the use of multiple distinct lip configurations. The lip configurations differ in diameter, shape and orientation. In the preferred embodiment the central portion of the mesh disc (i.e. the portion closest to the delivery element, such as the wire or deliver microcatheter) will be oriented parallel to the neck of the target aneurysm.

The diameter of the mesh disc ranges from 0.1 mm to 30 cm.

The shape of the mesh disc ranges from a circle to triangle. The shape is most typically round or oval.

In a typical spherical aneurysm with a narrow neck, the entire mesh disc 14 and at least one hole 200 in said mesh disc include the lips and should be oriented parallel to the neck of the target aneurysm. In this case, the lips overhang and rest on the base of the target aneurysm, completely covering the neck of the target aneurysm and extending over a portion of the adjacent base of the target aneurysm and forming a structure for least one hole 200.

In a typical non-spherical aneurysm with a wide neck, the entire outer perimeter of the mesh disc 14 should be oriented more perpendicular to the neck of the target aneurysm than in the case of the typical spherical aneurysm with a narrow neck, so as to gently grip the walls near the base of the target aneurysm.

Referring now to FIG. 1, control element 11 is the user interface that has the optional capability of sending signals through catheter element 12, sometimes termed delivery catheter 12, and/or along delivery microcatheter 13, sometimes termed a hypotube 13. In some cases, the "microcatheter" 13 may be solid (such as when microcatheter 13 is a wire). Control element 11 is deployed outside the body containing the target aneurysm. Control element 11 optionally deploys catheter 12 to a location proximal to the base of the neck of the target aneurysm 100. Said control element 11 is optionally attached to catheter element 12 and/or optionally attached to delivery microcatheter 13 disposed therein. Said control element 11 is capable of sending signals via catheter element 12 and/or delivery microcatheter 13 to detachment element 17. In the preferred embodiment control element 11 is a separate detachment tool that is applied to the proximal side of delivery microcatheter 13 at the desired time, in order to detach the mesh disc 14 from said delivery microcatheter 13. Prior to deployment, additional contrast or other fluid injections can optionally be used to initiate deployment of optional balloon(s) 303 or 300 for the purpose of positioning catheter 12 so as to center delivery microcatheter 13 for optimal deployment of mesh disc 14. Detachment element 17 in turn may relay signals to mesh disc element 14. Said relay signals are capable of initiating the decompression of said mesh disc 14 and at least one hole 200 in said mesh disc upon deployment. Alternatively, said compression may be automatic triggered by its release from constraints. Following deployment of said mesh disc 14 and at least one hole 200 in said mesh disc, control element 11 is optionally capable of sending signals which result in the deployment of coils 24, hydrogel 16, and/or lips 14A. In the preferred embodiment a separate control element 20 controls detachment of coils 24. Following deployment of the aforementioned elements, control element 11 is capable of signaling detachment element 17 to separate delivery microcatheter 13 from said mesh disc 14 and at least one hole 200 in said mesh disc. Control element 11 is then capable of retracting catheter 12 and delivery microcatheter 13. In the preferred embodiment, the control element 11 is commercially available.

In the preferred embodiment catheter 12 has an outer diameter ranging from 3 Fr. to 5 Fr.

Note that said mesh disc 14 and at least one hole 200 in said mesh disc will be held in position upon deployment by coils 24 or hydrogel 16, each of which will substantially conform to the interior of target aneurysm 100. Alternatively, mesh disc 14 must have up going "lips" and can be held in place by friction between said disc and the walls of the target aneurysm, as well as the fact that disc 14 has a greater diameter than the diameter of the aneurysmal neck. Lastly, a larger disc 14 can be held in place both ways.

Mesh disc 14 and at least one hole 200 in said mesh disc are compressible into a shape suitable for delivery through a catheter 12, and capable of expanding into a disc shape upon receipt of an electronic signal from control element 11, or upon release from its constraint. Said mesh 14 is capable of being coated with hydrogel 16, and holes in said mesh 14• are capable of storing said hydrogel 16 until deployment within said aneurysm 100.

The amount of said hydrogel 16 may vary. The specific amount is not significant as long as sufficient hydrogel 16 is deliverable to the aneurysm 100 to fill it. Typically, the smallest volume is approximately equivalent to a 3 mm sphere; the largest is approximately equivalent to an 8 mm sphere. In the preferred embodiment of the present invention the optional hydrogel coats mesh disc 14 and at least one hole 200 in said mesh disc such that the hydrogel will expand into and filling the aneurysm dome.

Mesh disc 14 and at least one hole 200 in said mesh disc are releasably attached to delivery microcatheter 13 by detachment element 17.

Mesh disc 14 and at least one hole 200 in said mesh disc are, in the preferred embodiment, radio-opaque or have radio-opaque marker or other positioning markers or incorporates other technology for remote visualization and location detection. The same characteristic is incorporated in detachment element 17.

Figure 2:
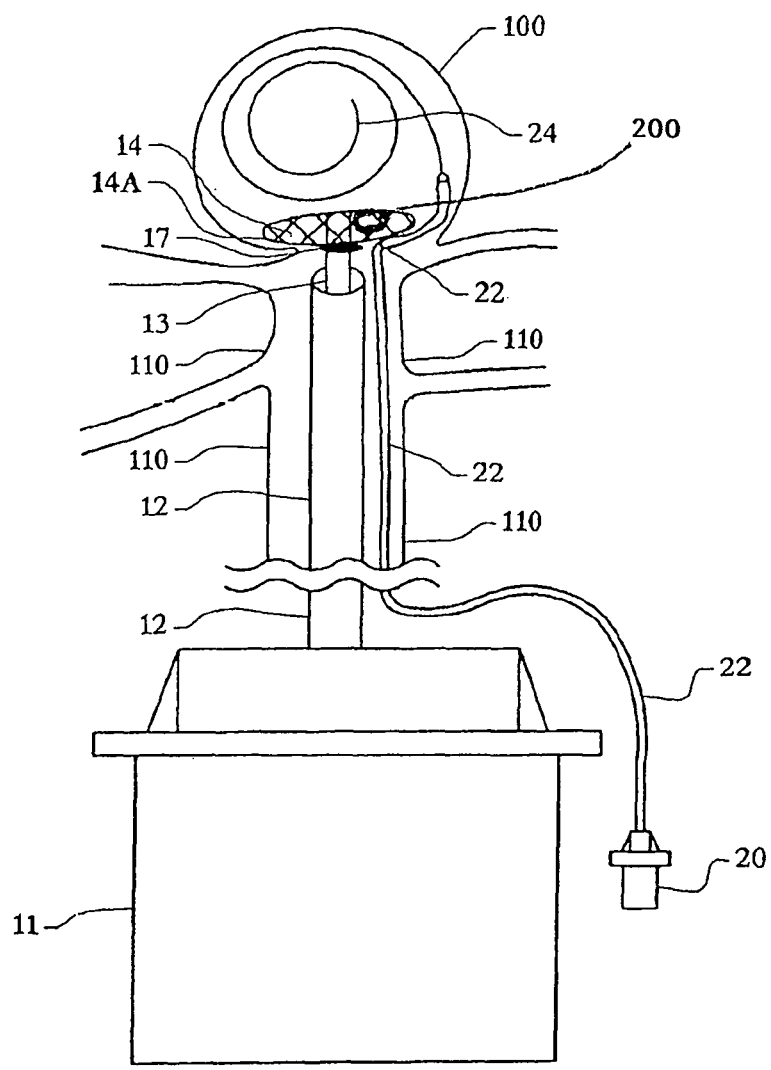
FIG. 2 depicts lips element 14A at periphery of flexible, substantially flat mesh disc 14 when uncompressed following delivery through and release from microcatheter 13 (said microcatheter 13 may be a solid wire, a microcatheter or a combination thereof) disposed within aneurysmal neck 100; along with a deployed prior art device composed of control element 20, catheter 22, wire coil 24 and at least one hole 200 in mesh disc 14 introduced into saccular aneurysm 100.

Referring now to FIG. 2, the mesh disc 14 and at least one hole 200 in said mesh disc are deployed through delivery catheter 12 passing through vessel 110 to the base of the neck of target saccular aneurysm 100. Control device 11 may optionally signal delivery microcatheter 13 to extend beyond the distal end of catheter 12 in a length sufficient to enter target aneurysm 100 to allow deployment of mesh disc 14 and at least one hole 200 in said mesh disc. Once the progress of delivery microcatheter 13 ceases, control element 11 signals mesh disc 14 and at least one hole 200 in said mesh disc to deploy. Mesh disc 14 and at least one hole 200 in said mesh disc enter the target aneurysm in a compacted form, said signal from control element 11 directs said mesh disc 14 and at least one hole 200 in said mesh disc to open as a blossom to allow the perimeter of said mesh disc 14 and at least one hole 200 in said mesh disc to overlap the base of the neck of the aneurysm 100. In the preferred embodiment the delivery catheter 12 is manually held in place while the delivery microcatheter 13 is manually advanced forward in a length sufficient to enter target aneurysm 100 to allow deployment of mesh disc 14 and at least one hole 200 in said mesh disc. Mesh disc 14 and at least one hole 200 in said mesh disc enter the target aneurysm in a compacted form and as it is released from its constraint said mesh disc 14 and at least one hole 200 in said mesh disc open as a blossom to allow the perimeter of said di mesh disc 14 and at least one hole 200 in said mesh disc to overlap the base of the neck of the aneurysm 100. The disc is then gently pulled back manually into position, which is determined preferentially by fluoroscopic and/or angiographic images.

The present invention employs a control element 11. Said control element's function is to detach mesh disc 14 and at least one hole 200 in said mesh disc at a specific time. Control element 11 may be combined with control elements of various devices which may be used with the present invention. Control element 11 may incorporate mechanical, chemical, hydrostatic, electrical and/or thermal means for implementing the function of detaching mesh disc 14 and at least one hole 200 in said mesh disc.

Continuing to refer to FIG. 2, such deployment can accompany the deployment of existing devices which disrupt the flow across the aneurysmal neck, such as prior art coil 24 in the saccular aneurysm as illustrated in FIG. 2 deployed by a second control element 20 through second catheter 22. It should be noted that mesh disc element 14 of the present invention is capable of resulting in a second "jailed" microcatheter.

Figure 3:
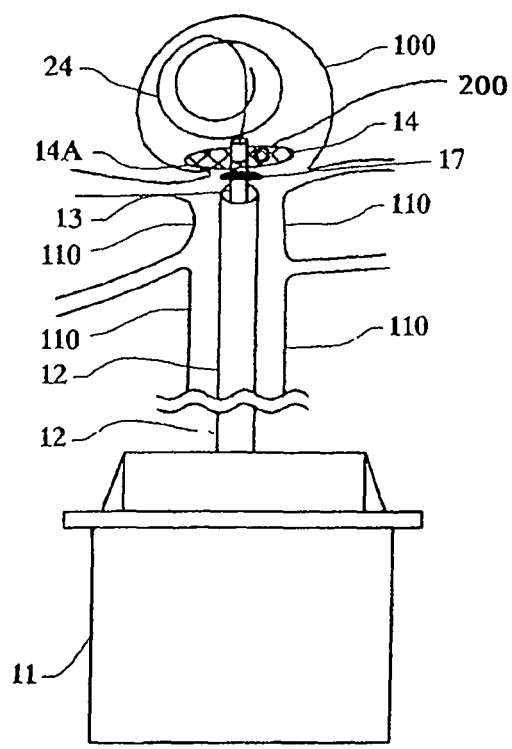
FIG. 3 depicts the present invention 10 deployed through vessel 110 with mesh disc 14 deployed at base of neck of a target spherical aneurysm 100, integrating wire coil element 24 of the prior art and at least one hole 200 in mesh disc 14.

Referring now to FIG. 3, the present invention may incorporate elements of the prior art, such as the deployment of coils 24 through microcatheter 13.

Figure 3A:
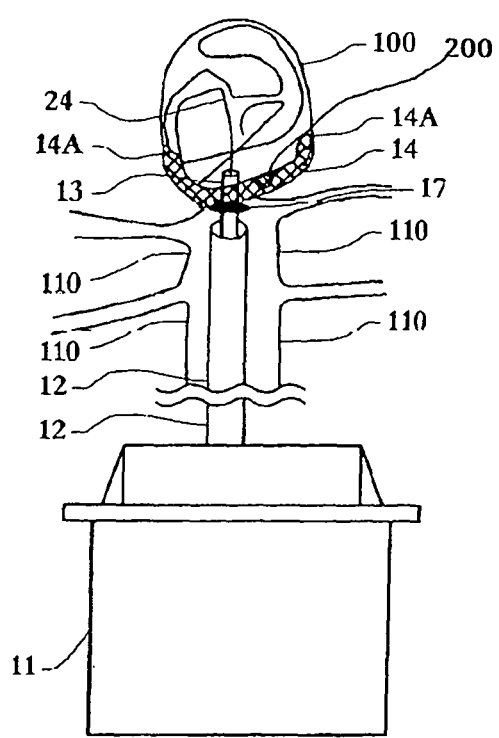
FIG. 3A depicts the present invention 10 deployed through vessel 110 with mesh disc 14 deployed at base of neck of a targeted, non-spherical aneurysm 100, integrating wire coil element 24 of the prior art.

Referring now to FIG. 3A, the present invention teaches the use of up turned lips to secure said mesh disc.

Figure 4:
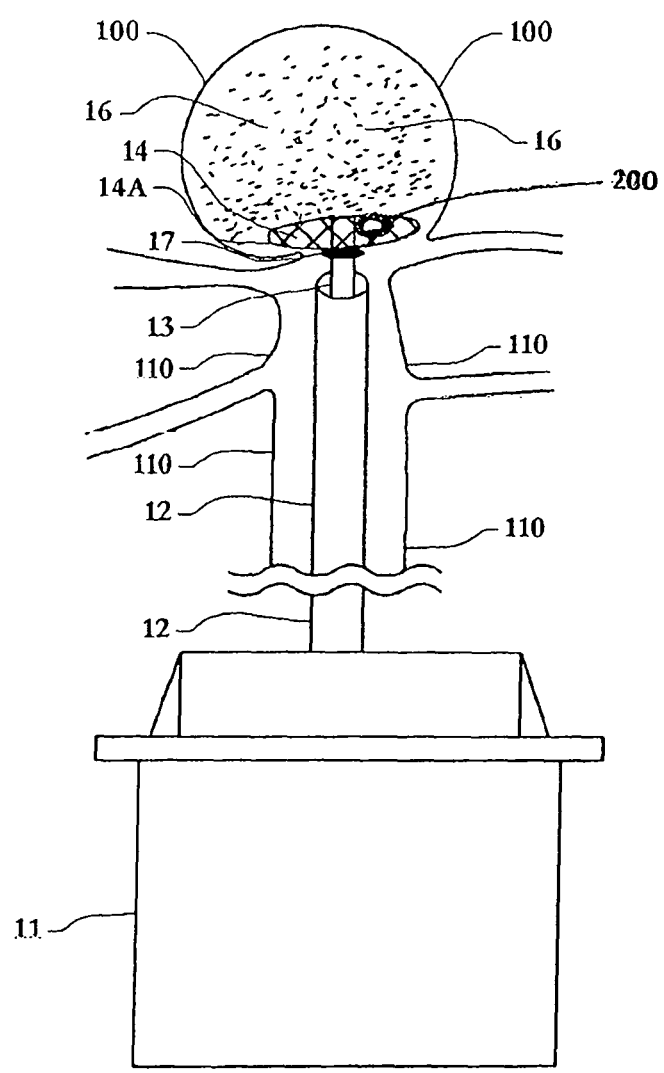
FIG. 4 illustrates an alternate embodiment of the present invention, deploying at least one hole 200 in mesh disc 14 in conjunction with activated (i.e., swollen) hydrogel 16 within target aneurysm 100.

Referring now to FIG. 4, an alternate embodiment of the present invention deploys mesh disc 14 and at least one hole 200 in said mesh disc in conjunction with semitransparent, activated/swollen hydrogel 16. Hydrogel 16 can be deployed on the surface of mesh disc 14 and at least one hole 200 in said mesh disc, via a hollow in delivery microcatheter 13, via a second device (not shown), or via a second wire (not shown) deployed through catheter element 12. Alternatively, the hydrogel 16 may be deployed via the mesh disc 14 and at least one hole 200 in said mesh disc. Alternatively, hydrogel embedded coils may be used with the present invention.

Figure 5:
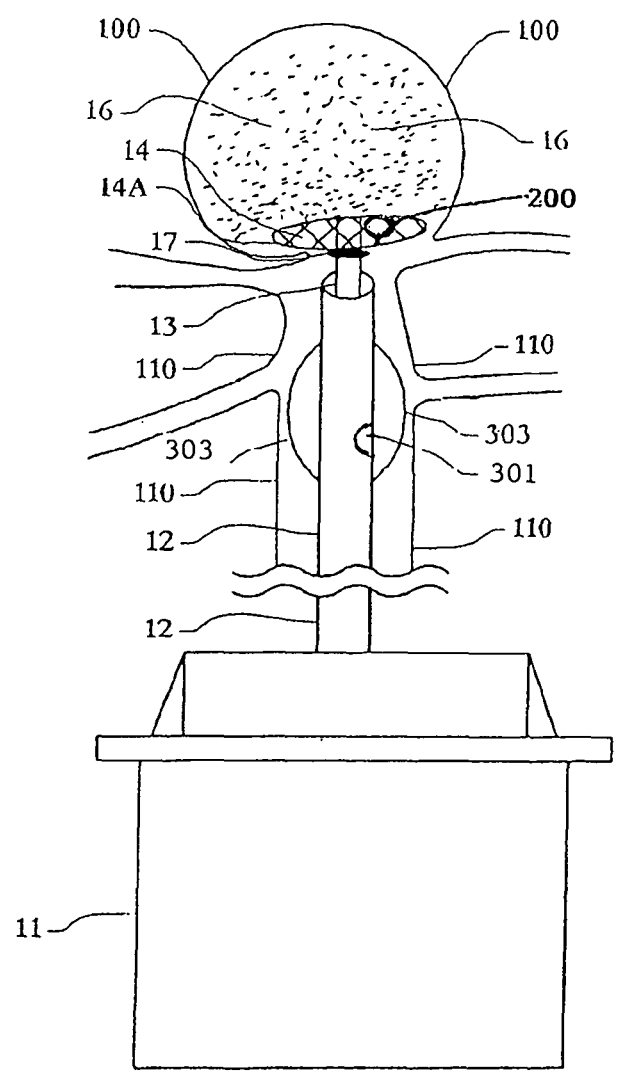
FIG. 5 depicts an alternate embodiment of the hydrogel 16 impregnated device including the at least one hole 200 in mesh disc 14 of FIG. 4, further including optional centering balloon 303 to position catheter element 22 more precisely in relation to the center of the neck of target aneurysm 100.

Referring now to FIG. 5, an alternate embodiment of FIG. 4 further includes a centering balloon 303 within vessel 110. Centering balloon 303 allows catheter element 12 to be positioned more precisely and stably in relation to the center of the neck of target aneurysm 100. Referring more particularly to centering balloon 303, said balloon is described in detail in Walzman application Ser. No. 15/482,436 (entitled Vessel access catheter), incorporated herewith by reference.

It should be noted that Walzman application Ser. No. 15/482,436 (entitled Vessel access catheter), incorporated herewith by reference describes both single balloons and balloon arrays. The present invention's centering balloon 303 may be either a single balloon or a balloon array. Said single balloon or balloon arrays are designed to help center the tip of catheter element 12 to a location proximal to the center of the target aneurysm. Said positioning may be achieved by the inflation of at least one balloon in order to deflect catheter element 12 in a desired direction.

Figure 6:
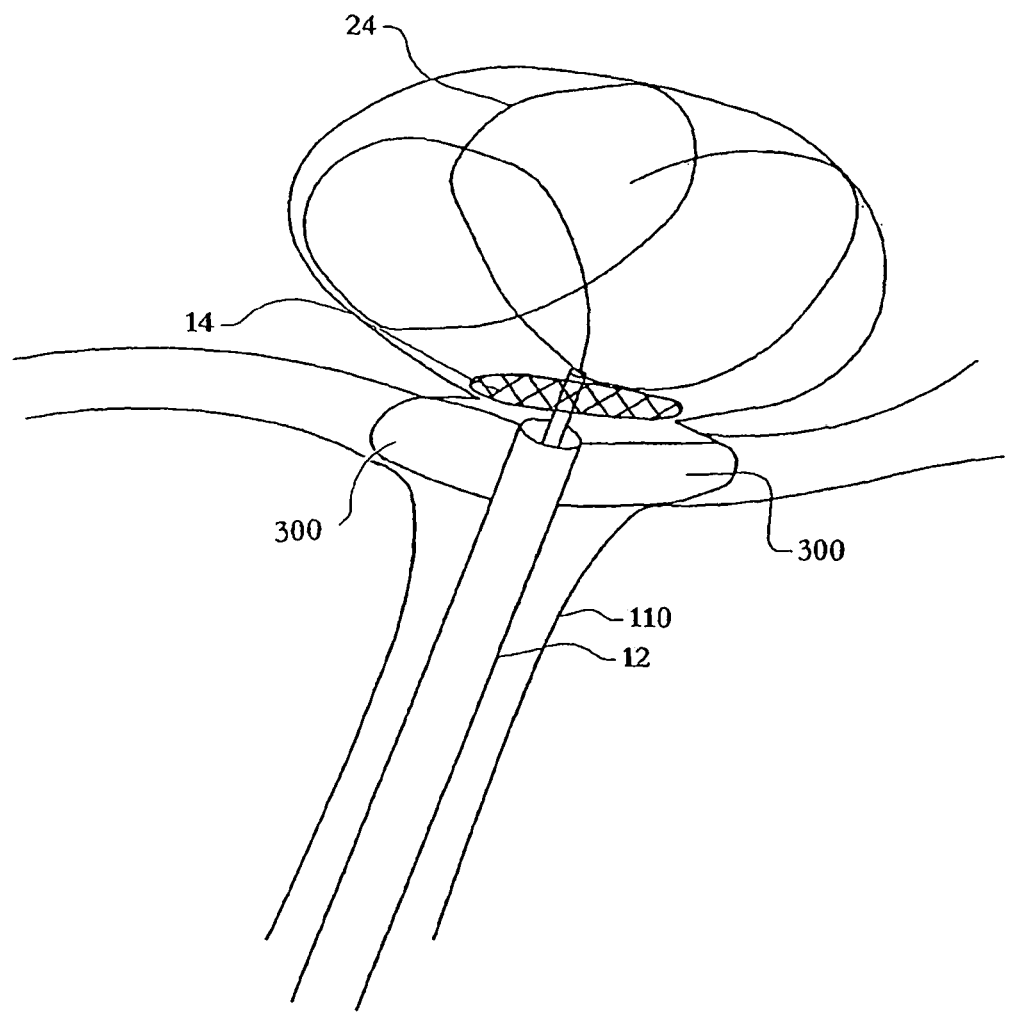
FIG. 6 illustrates a detailed deployment of the optional disc balloon 3

An additional embodiment of the current invention incorporates the Walzman disc balloon 300, as illustrated by FIG. 6, into catheter element 12. Said incorporation is an alternate embodiment which is designed to help center the tip of catheter element 12 to a location proximal to the center of the target aneurysm. It may also act as vertical positioning element by abutting the base of the mesh disc during positioning in the target aneurysm.

Both balloon embodiments separately or in combination are also designed to arrest flow within the vessel proximate to the target aneurysm when fully inflated. Said inflation will result in control of unwanted bleeding in case of target aneurysm rupture.

Thus, the present invention can have several different embodiments, including:

First, a disc alone—an appropriately sized disc can be deployed through a microcatheter in a saccular aneurysm, after a second microcatheter is placed in the microcatheter. The disc is gently pulled back to the neck of the aneurysm, bridging said neck, and with a lip beyond the open portion of the neck to stabilize the disc. The disc is not detached at first, but remains tethered to its delivery system (a wire or catheter). Were it to be deployed early it would likely migrate into the aneurysm and be ineffective and sometimes dangerous. Through the second microcatheter, which is now "jailed" in the aneurysm, appropriately sized coils are sequentially placed and deployed into the aneurysm per current routine protocols/techniques, until the aneurysm is adequately filled with coils. The second microcatheter is removed. At this point the disc is detached from its delivery wire/catheter, which is removed.

Second, a disc mounted on a hypotube or microcatheter 13 which is introduced into aneurysm through a slightly larger catheter, wherein the hypotube or microcatheter goes through the disc to just beyond it. An appropriately sized disc can be deployed through a microcatheter in a saccular aneurysm. The disc is gently pulled back to the neck of the aneurysm, bridging said neck, and with a lip beyond the open portion of the neck to stabilize the disc. The disc is not detached at first but remains tethered to its delivery catheter/hypotube. Were it to be detached early it would likely migrate into the aneurysm and be ineffective and sometimes dangerous. Through said delivery catheter/microcatheter appropriately sized coils are sequentially placed and deployed into the aneurysm per current routine protocols/techniques, until the aneurysm is adequately filled with coils. At this point the disc is detached from its catheter/hypotube. The catheter/hypotube is then removed.

Third, a hydrogel enhanced disc alone. The disc is an endovascularly deployed mesh composed of a shape-memory material such as nickel-titanium alloy or other memory-shape material capable of super-elastic properties, such that the compressed mesh disc will revert to its flat-mesh disc shape upon release or activation by an electronic or light impulse. It will optionally have two layers like to inner disc of the Anplatz Left Atrial Appendage closure device currently in trials—the disc can have versions that are relatively flat, or some versions where the edges are folded up to accommodate different shape aneurysms, including very wide neck aneurysm. In this version, however, the outside surface of the disc facing into the aneurysm is lined with a non-biodegradable hydrogel, that when exposed to blood upon deployment, will swell over a prescribed time (10 minutes in the preferred embodiment of the present invention), to conform to the size and shape of the aneurysm, and fill and occlude said aneurysm. The other layer of the disc that is closer to the parent artery can optionally have thin layers of hydrogel as well—but this layer would have hydrogel designed only to swell to occlude that layer of disc alone, so no hydrogel from the other layer can potentially expand through the mesh into the parent vessel. An appropriately sized disc can be deployed through a microcatheter in a saccular aneurysm. The disc is gently pulled back to the neck of the aneurysm, bridging said neck, and with a lip beyond the open portion of the neck to stabilize the disc. The disc is not detached at first but remains tethered to its delivery system (a wire or catheter). Were it to be detached early it would likely migrate into the aneurysm and be ineffective and sometimes dangerous. The disc is held in place at the neck of the aneurysm, while the hydrogels swell. Once the prescribed time is elapsed and follow up angiography confirms occlusion of the aneurysm, the disc is detached from its delivery wire/catheter, and the delivery wire/catheter and the microcatheter through which it was deployed are removed. The hydrogel fills the aneurysm, which occludes that aneurysm and also stabilizes the disc in place (in example 1 and 2 above the coils achieve these 2 goals).

Fourth, all features of the first through third above and optionally; plus the disc can have a smaller metal core disc that is smaller than the diameter of the aneurysm and has hydrogel designed to expand out in a disc like shape from the edges, to make a larger disc that can then be gently dragged into position. It can then be pinned in place by coils or optional hydrogel embedded in the top of the disc, that also then expands into the dome of the aneurysm, either via a layer on the top of the metal disc designed to expand after the side hydrogel, or via a separately implanted hydrogel bead or the like.

Fifth, instead of the metal disc that expands in diameter via hydrogel, one may employ an all hydrogel disc on a pusher wire or hypotube/catheter and expands in a flat disc shape to various pre-programmed diameters and/or shapes.

The mesh disc 14 and at least one hole 200 in said mesh disc may also optionally be delivered through a disc balloon microcatheter (previously described by Walzman Ser. No. 15/732,170) or a similar configuration (disc balloon), an intermediate catheter, or another balloon catheter. These can serve as methods for delivering the present invention. Said method(s) may also be used to deliver any mesh intrasaccular device including other devices taught by the prior art, such as the Web and the Luna.

The advantage of a delivery through a disc balloon microcatheter is twofold. First, the balloon may sometimes be helpful positioning the mesh disc 14 and at least one hole 200 in said mesh disc, and second, that in the event the aneurysm ruptures during treatment, the balloon can be inflated to arrest flow and control active bleeding until more coils can be placed and/or the hydrogel swells to seal the aneurysm.

Said disc and said coil loops vary in size and in the time necessary to fully deploy. More particularly, the diameter of said discs vary from 0.1 mm-500 mm. The diameter of said coil loops vary from 0.1 mm-1000 mm. The length of said coil loops can be 0.1 mm-3142 mm long Coil loops for coil invention are typically sized in diameter of the target aneurysm.

With respect to the time necessary to fully deploy said disc and said coil vary from nearly instantaneous [approximately one second or less] to 1 hour. While in some embodiments both said disc and said coil expand at the same rate, in other embodiments said disc and said coil expand at independent rates. In some embodiments said coil expands faster than said disc and in other embodiments said disc expands faster than said coil.

In the preferred embodiment said coils complete their expansion approximately forty-five (45) seconds after said disc completes its expand. This time off set allows the present invention to be positioned into optimal position across neck (the opening) of the target aneurysm without dragging metal under outward tension along said target aneurysm or vessel walls thus eliminating or ameliorating medical difficulties such as breaching said aneurysm or said vessel walls. Said breaches can result in injury or death to a patient.

The present invention has four structural optional elements. Said optional element are central donut holes in the disc element of the present invention; single or multiple mesh layer(s) in the disc element of the present invention; hydrogel coating on all or parts of the disc element of the present invention; and hydrogel coating of all or parts of the surface(s) of at least one hole 200 of the present invention More particularly, the donut hole structure in the disc element of the present invention is optional. One embodiment of the present invention has a central donut hole structure. Another embodiment of the present invention does not have a central donut hole structure.

More specially, the single layered mesh configuration of the present configuration is optional. One embodiment of the present invention has a single mesh layer in the disc element of the present invention. Another embodiment of the present invention the present invention has multiple mesh layers in the disc element of the present invention.

More expressly, the application of a hydrogel coating of the disc element of the present invention is optional. One embodiment of the present invention discloses a hydrogel coating on the surfaces of the disc element of the present invention. In another embodiment of the present invention said hydrogel coating is not applied to the surfaces of the disc element of the present invention. In other embodiments, a hydrogel coating is employed on some but not all surfaces of the mesh disc. In some optional embodiments the hydrogel is chemically optimized to expand significantly, and may also be positioned so that it expand, into the pathological outpouching, to further aid in the thrombosis/closure of said aneurysm/outpouching.

More especially, the application of a hydrogel coating of the at least one hole 200 in mesh disc 14 of the present invention is optional. One embodiment of the present invention discloses a hydrogel coating on the surfaces of the at least one hole 200 in mesh disc 14 of the present invention. In another embodiment of the present invention said hydrogel coating is not applied to some of the surfaces of the at least one hole 200 in mesh disc 14 of the present invention. In yet another embodiment of the present invention said hydrogel coating is not applied to any of the surfaces of the at least one hole 200 in mesh disc 14 of the present invention.

Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

What is claimed is:

1. An embolic device configured for ameliorating bodily outpouchings, comprising a control element, a catheter element, a delivery microcatheter hypotube, a detachment element, a flattened mesh disc, a distal opening and at least one hole in said mesh disc;
    wherein said catheter element further comprises at least one side hole; further comprising at least two centering balloon deployed via said at least one side hole; and
    wherein said mesh disc further comprises a proximal face and a distal face, said proximal face being opposite of said distal face; and
    said proximal face and said distal face are substantially flat; and
    wherein said mesh disc upon deployment is disposed distally and is configured to be in communication with an aneurysmal neck; and
    wherein said mesh disc further comprises peripheral lips are configured to be oriented parallel to said aneurysmal neck;
    wherein said peripheral lips are configured to overhang and rest on a base of said aneurysmal neck.

2. The device of claim 1, wherein said mesh disc is flexible.

3. The device of claim 1, wherein said delivery hypotube further comprises a channel capable of delivering at least one coil therethrough.

4. The device of claim 1, wherein said mesh disc is capable of deploying hydrogel in a sufficient amount to fill said outpouchings.

5. The device of claim 4, wherein said hydrogel is delivered through said delivery hypotube for deployment by said mesh disc.

6. The device of claim 1, wherein said mesh disc is impregnated with said hydrogel in a sufficient amount to substantially fill said outpouchings.

7. An embolic device for ameliorating bodily outpouchings, comprising a control element, a catheter element, a wire, a detachment element, a mesh disc and a distal opening;
   wherein said catheter element further comprises at least one side hole; further comprising at least two centering balloon deployed via said at least one side hole; and
   wherein said mesh disc further comprises a proximal face and a distal face, said proximal face being opposite of said distal face; and
   said proximal face and said distal face are substantially flat;
   wherein said mesh disc upon deployment is disposed distally and is configured to be in communication with an aneurysmal neck; and
   wherein said mesh disc further comprises peripheral lips are configured to be oriented parallel to said aneurysmal neck;
   wherein said peripheral lips are configured to overhang and rest on a base of said aneurysmal neck.

8. The device of claim 7, wherein said mesh disc is flexible.

9. The device of claim 7, wherein said mesh disc is capable of deploying hydrogel in a sufficient amount to fill said outpouchings.

10. The device of claim 7, wherein said mesh disc is impregnated with said hydrogel in a sufficient amount to substantially fill said outpouchings.

11. The device of claim 7, wherein the periphery of said mesh disc is upturned.

12. The device of claim 7, wherein said mesh disc is configured to be positioned at the neck of bodily outpouchings.

13. The device of claim 12, wherein said mesh disc is configured not to substantially fill said bodily outpouchings.

* * * * *